United States Patent
Palmer et al.

(10) Patent No.: US 10,058,409 B2
(45) Date of Patent: Aug. 28, 2018

(54) SPACER FABRIC MESH FOR USE IN TISSUE ENGINEERING APPLICATIONS

(71) Applicant: MX Orthopedics, Corp., Billerica, MA (US)

(72) Inventors: Matthew Palmer, Cambridge, MA (US); Matthew Fonte, Concord, MA (US)

(73) Assignee: Arthrex, Inc., Naples, FL (US)

( * ) Notice: Subject to any disclaimer, the term of this patent is extended or adjusted under 35 U.S.C. 154(b) by 798 days.

(21) Appl. No.: 14/030,695

(22) Filed: Sep. 18, 2013

(65) Prior Publication Data

US 2014/0081296 A1 Mar. 20, 2014

Related U.S. Application Data (60) Provisional application No. 61/702,315, filed on Sep. 18, 2012, provisional application No. 61/708,141, filed on Oct. 1, 2012.

(51) Int. Cl.
*A61F 2/00* (2006.01)

(52) U.S. Cl.
CPC .................. *A61F 2/0063* (2013.01)

(58) Field of Classification Search
CPC ............ A61F 2/0063; A61F 2002/0068; A61F 2/0077; A61F 2/08; A61F 2/28; A61F 2/30; A61F 2002/009
USPC .................................................. 424/424, 443
See application file for complete search history.

(56) References Cited

U.S. PATENT DOCUMENTS

| | | |
|---|---|---|
| 3,906,550 A | 9/1975 | Rostoker et al. |
| 4,536,894 A | 8/1985 | Galante et al. |
| 4,636,219 A | 1/1987 | Pratt et al. |
| 4,693,721 A | 9/1987 | Ducheyne |
| 4,863,475 A | 9/1989 | Anderson et al. |
| 4,975,230 A | 12/1990 | Pinkhasov |
| 5,011,638 A | 4/1991 | Pinkhasov |
| 5,198,308 A | 3/1993 | Shetty et al. |
| 5,282,861 A | 2/1994 | Kaplan |
| 5,385,036 A | 1/1995 | Spillane et al. |
| 5,926,685 A | 7/1999 | Krebs et al. |
| 5,986,169 A | 11/1999 | Gjunter |

(Continued)

FOREIGN PATENT DOCUMENTS

WO 2011155824 12/2011

OTHER PUBLICATIONS

Ventral Hernia Repair System, Covidien, 2011, www.covidien.com/imageServer.aspx/doc212851.pdf?contentID=20762&contenttype=application/pdf.

(Continued)

*Primary Examiner* — Eric Rosen
*Assistant Examiner* — Chima Igboko
(74) *Attorney, Agent, or Firm* — Carlson, Gaskey & Olds, P.C.

(57) ABSTRACT

A spacer fabric mesh comprising:
 a spacer fabric comprising:
  a bottom fabric layer;
  a top fabric layer; and
  an intermediate layer comprising a plurality of interconnecting fibers which extend between, and connect, said bottom layer and said top layer, wherein said interconnecting fibers have sufficient resilience and stiffness to keep said bottom layer and said top layer separated when pressure is applied to at least one of said bottom layer and said top layer.

24 Claims, 11 Drawing Sheets

(56) References Cited

U.S. PATENT DOCUMENTS

| | | | |
|---|---|---|---|
| 6,042,592 A * | 3/2000 | Schmitt | A61F 2/0063 606/151 |
| 6,055,676 A | 5/2000 | Bainbridge et al. | |
| 6,087,553 A | 7/2000 | Cohen et al. | |
| 6,103,149 A | 8/2000 | Stankiewicz | |
| 6,120,539 A * | 9/2000 | Eldridge | A61F 2/0063 600/37 |
| 6,827,743 B2 * | 12/2004 | Eisermann | A61B 17/68 623/23.54 |
| 6,913,622 B2 | 7/2005 | Gjunter | |
| 6,929,866 B1 | 8/2005 | Williams et al. | |
| 7,169,720 B2 | 1/2007 | Etchells et al. | |
| 7,458,991 B2 | 12/2008 | Wang et al. | |
| 7,578,851 B2 | 8/2009 | Dong et al. | |
| 7,875,070 B2 | 1/2011 | Molaei | |
| 7,883,661 B2 | 2/2011 | Hamman et al. | |
| 7,976,648 B1 | 7/2011 | Boylan et al. | |
| 8,062,378 B2 | 11/2011 | Fonte | |
| 8,216,398 B2 | 7/2012 | Bledsoe et al. | |
| 8,425,588 B2 | 4/2013 | Molaei | |
| 8,585,770 B2 | 11/2013 | Meridew et al. | |
| 8,721,646 B2 | 5/2014 | Fox | |
| 9,017,331 B2 | 4/2015 | Fox | |
| 9,339,268 B2 | 5/2016 | Fox | |
| 2002/0198601 A1 * | 12/2002 | Bales | A61B 17/80 623/23.55 |
| 2005/0113938 A1 * | 5/2005 | Jamiolkowski | A61F 2/02 623/23.74 |
| 2005/0142971 A1 | 6/2005 | Chen et al. | |
| 2006/0015183 A1 | 1/2006 | Gilbert et al. | |
| 2007/0116734 A1 | 5/2007 | Akash | |
| 2008/0091277 A1 * | 4/2008 | Deusch | A61B 17/0057 623/23.74 |
| 2008/0177378 A1 * | 7/2008 | Asgari | A61L 27/427 623/1.38 |
| 2009/0126413 A1 | 5/2009 | Sorensen et al. | |
| 2009/0288312 A1 | 11/2009 | Dua | |
| 2010/0292791 A1 * | 11/2010 | Lu | A61K 38/18 623/13.12 |
| 2011/0229685 A1 | 9/2011 | Lin et al. | |
| 2011/0245930 A1 | 10/2011 | Alley et al. | |
| 2012/0297526 A1 | 11/2012 | Leon | |
| 2014/0081296 A1 | 3/2014 | Palmer et al. | |
| 2014/0223649 A1 | 8/2014 | Fowler et al. | |
| 2014/0257420 A1 | 9/2014 | Fox | |
| 2014/0324048 A1 | 10/2014 | Fox | |

OTHER PUBLICATIONS

Bauer, Thomas W et al, Hydroxyapatile-Coated Femoral Stems, The Journal of Bone and Joint Surgery, Dec. 1991, pp. 1439-1452, vol. 73-A(10).

Coathup, M J et al, A comparison of bone remodeling around hyroxyapalite-coated, porous-coated and grit-blasted hip replacements retrieved at post-mortem, The Journal of Bone & Joint Surgery (Br), Jan. 2001, pp. 118-123, vol. 83-B(1).

Galante, Jorge et al., Sintered Fiber Metal Composites as a Basis for Attachment of Implants to Bone, Jan. 1971, pp. 101-144, vol. 53-A(1).

Harris, William H. et al., Total Hip and Total Knee Replacement, The New England Journal of Medicine, 1990, pp. 801-807, vol. 323(12).

Landon, Glenn C., Noncemented Total Knee Arthroplasty, Clinical Orthopedics and Related Research, Apr. 1986, pp. 49-57, vol. 205.

Lembert, E. et al., Fixation of Skeletal Replacement by Fiber Metal Composites, Clinical Orthopedics and Related Research, Sep. 1972, pp. 303-310, vol. 87.

Mayman, David J. et al., Late Fiber Metal Shedding of the First and Second-Generation Harris Galante Acetabular Component. A Report of 5 Cases, The Journal of Arthroplasty, Jun. 2007, pp. 624-629, vol. 22(4).

Nelson, Carl L., A Comparison of Gentamicin-Impregnated Polymethylmethacrylate Bead Implantation to Conventional Parenteral Antibiotic Therapy in Infected Total Knee and Hip Arthroplasty, Clinical Orthopedics and Related Research, Oct. 1993, pp. 96-101, vol. 295.

Pidhorz, Laurent E., et al., A Quantiative Study of Bone and Soft Tissues in Cementless Porous-coated Acetabular Components Retrieved at Autopsy. The Journal of Arthroplasty, Apr. 1993, pp. 13-225,vol. B(2).

Spector, Myron, Historical Review of Porous-coated Implants, The Journal of Arthroplasty, Jun. 1987, pp. 163-177, vol. 2(2).

Tonino, Alphons J. et al., Hydroxyapalite-coated femoral stems: Histology and Histomorphometry Around Five Components Retrieved at Post Mortem, The Journal of Bone & Joint Surgery (Br), Jan. 1999, pp. 148-154, vol. 81-B(1).

Venesmaa, Petri K. et al., Monitoring of Periprosthetic BMD After Uncemented Total Hip Arthroplasty with Dual-Energy X-Ray Absorptiometry—a 3-Year Follow-Up Study, Journal of Bone and Mineral Research, 2001, pp. 1056-1061, vol. 16(6).

Orthopedic Network News, 2010 Hip and Knee Implant Review, Jul. 2010, pp. 1 and 3, vol. 21(3).

Lueck, Roger A. e al., Development of an Open Pore Metallic Implant to Permit Attachment to Bone, Orthopedic Surgery, 1969, pp. 456-457.

Gustilo, Ramon B. et al., Revision Total Hip Arthroplasty with Titanium Ingrowth Prosthesis and Bone Grafting for Failed Cemented Femoral Component Loosening, Clinical Orthopaedics and Related Research, Oct. 1988, pp. 111-119, vol. 235.

Sumner, D. R. et al., Remodeling and Ingrowth of Bone at Two Years in a Canine Cementless Total Hip-Arthroplasty Model, The Journal of Bone and Joint Surgery, Feb. 1992, pp. 239-250, vol. 74-A(2).

Urban, Robert M. et al., The Bone-Implant Interface of Femoral Stems with Non-Circumferential Porous Coating, The Journal of Bone and Joint Surgery, 1996, pp. 1068-1081.

Hreljac, Alan, Impact and Overuse Injuries in Runners, Medicine & Science in Sports & Exercise, 2004, pp. 545-849.

Milner, Clare E. et al., Biomechanical Factors Associated with Tibial Stress Fracture in Female Runners, Medicine & Science in Sports & Exercise, 2006, pp. 323-328.

Nigg, B.M. et al., Effect of viscoelastic shoe insoles on vertical impact forces in heel-toe running, The American Journal of Sports Medicine, 1988, pp. 70-76, vol. 16, No. 1.

House, Carol M. et al., User Trial and Insulation Tests to Determine Whether Shock-Absorbing Insoles are Suitable for Use by Military Recruits during Training, Military Medicine, Sep. 2004, pp. 741-746, vol. 169.

James, Stanley L. et al., Injuries to runners, The American Journal of Sports Medicine, 1978, pp. 40-50, vol. 6, No. 2.

Pratt, D.J., Medium term comparison of shock attenuating insoles using a spectral analysis technique, J. Biomed. Eng., Oct. 1988, pp. 426-429, vol. 10.

Liu, Yanping et al., Compression behavior of warp-knitted spacer fabrics for cushioning applications, Textile Research Journal, Aug. 2, 2011, pp. 1-10.

* cited by examiner

SPACER FABRIC MESH FOR USE IN TISSUE ENGINEERING APPLICATIONS

REFERENCE TO PENDING PRIOR PATENT APPLICATIONS

This patent application claims benefit of:

(i) prior U.S. Provisional Patent Application Ser. No. 61/702,315, filed Sep. 18, 2012 by Matthew Palmer et al. for SPACER FABRICS FOR TISSUE ENGINEERING APPLICATIONS; and (ii) prior U.S. Provisional Patent Application Ser. No. 61/708,141, filed Oct. 1, 2012 by Matthew Palmer et al. for SPACER FABRICS FOR TISSUE ENGINEERING APPLICATIONS.

The two (2) above-identified patent applications are hereby incorporated herein by reference.

FIELD OF THE INVENTION

This invention relates to tissue engineering in general, and more particularly to tissue engineering using spacer fabrics.

BACKGROUND OF THE INVENTION

Biologic and synthetic meshes are used to reinforce and/or repair damaged tissues. Biologic meshes are generally derived from tissues that have been de-cellularized and sterilized. Synthetic meshes are generally woven or knit from polymers. Biologic and synthetic meshes are widely used in tissue engineering applications to treat hernias, to reinforce and/or repair ligaments, tendons and/or muscles (including the rotator cuff in the shoulder the capsule of the hip joint, the capsule of the knee joint, etc.), and to treat chronic ulcerations of soft tissues.

Biologic Meshes

Figure 1:
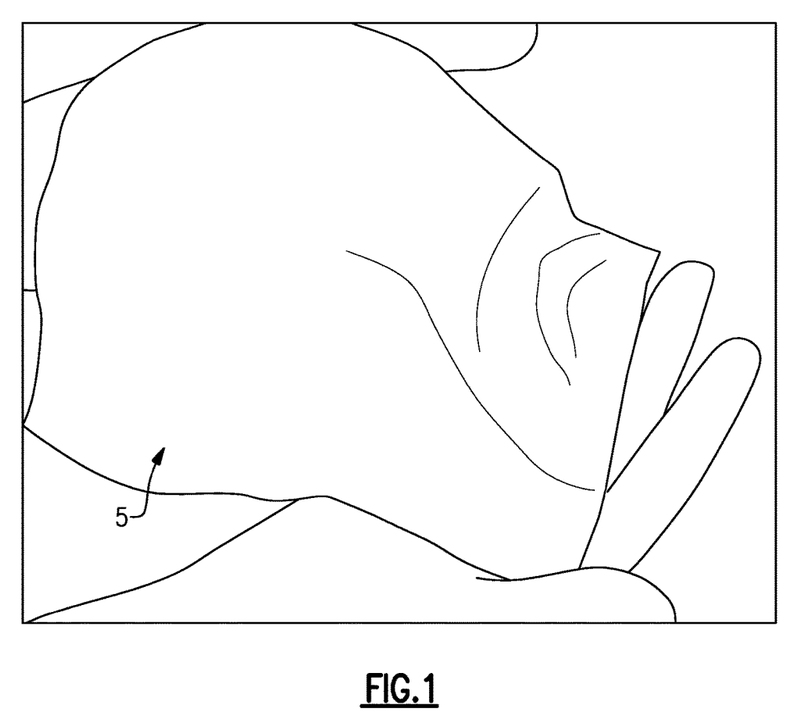
FIG. 1 is a schematic view showing a conventional biologic mesh formed from collagen extracellular matrix.

Biologic meshes are typically derived from human, porcine, bovine and/or equine tissue. More particularly, the source tissue (e.g., dermis, pericardium, small intestine submucosa, etc.) is first treated so as to remove cellular and DNA material, leaving essentially the extracellular matrix. This extracellular matrix, which is predominantly collagen, is then formed into the biologic mesh. If desired, the biologic mesh may be further processed (e.g., crosslinked) in order to increase its strength, and then it is terminally sterilized. The biologic mesh is often lyophilized in order to prolong its shelf-life. When the biologic mesh is to be used, it is re-hydrated with a saline solution or other biologically-active agent. See FIG. 1, which shows a biologic mesh 5 formed from extracellular matrix.

Synthetic Meshes

Synthetic meshes are typically manufactured from polymer fibers which are woven or knit together so as to create a porous two-dimensional structure. The polymer fibers may be absorbable or permanent. The polymers used to form a conventional synthetic mesh typically include:

Polyglactin (for an absorbable mesh)
Polyglycolic acid (for an absorbable mesh)
Polypropylene (for a non-absorbable mesh)
Polyester (for a non-absorbable mesh)
ePTFE (for a non-absorbable mesh)

Figure 2:
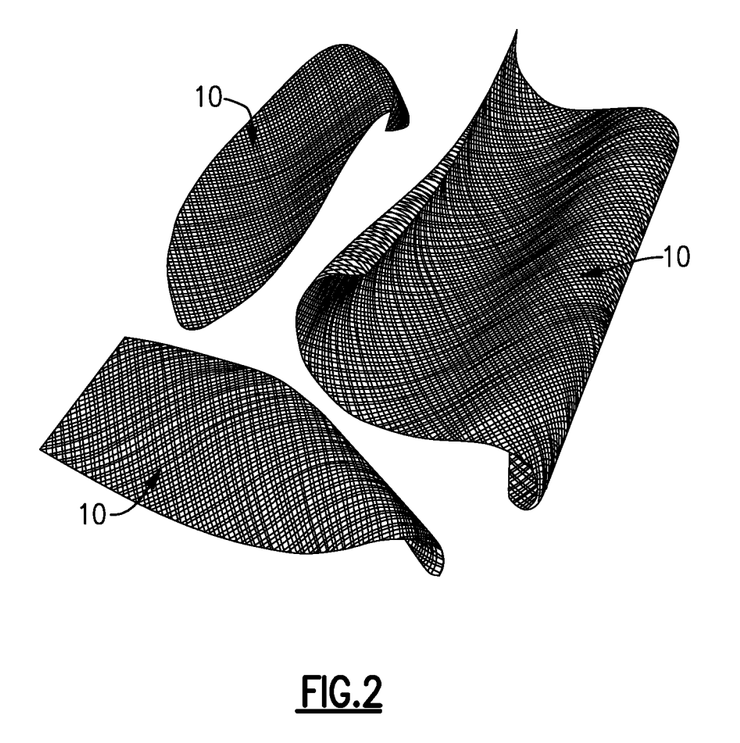
FIG. 2 is a schematic view showing a conventional knit surgical mesh.

The pore size of the mesh can be controlled during the knitting or weaving process and typically varies from about 0.4 mm to about 3.6 mm. Additionally, depending on how the mesh is manufactured, the mesh may have varying degrees of stretch and/or flexibility. See FIG. 2. which shows a conventional synthetic mesh 10 formed by weaving or knitting together polymer fibers.

Herniations

A herniation occurs when tissue (e.g., an organ) protrudes through a wall that normally contains it. A hernia may result when the pressure in the compartment of the residing tissue (e.g., the organ) is increased, and the containing membranes or muscles are weak or weakened. Such weakening of the containing membranes or muscles is frequently congenital, although some medical conditions can increase intra-compartmental pressure (e.g., pregnancy can increase intra-abdominal pressure) and thus may result in hernias. Common hernias include:

Inguinal
Femoral
Umbilical
Incisional
Diaphragmatic

Figure 3:
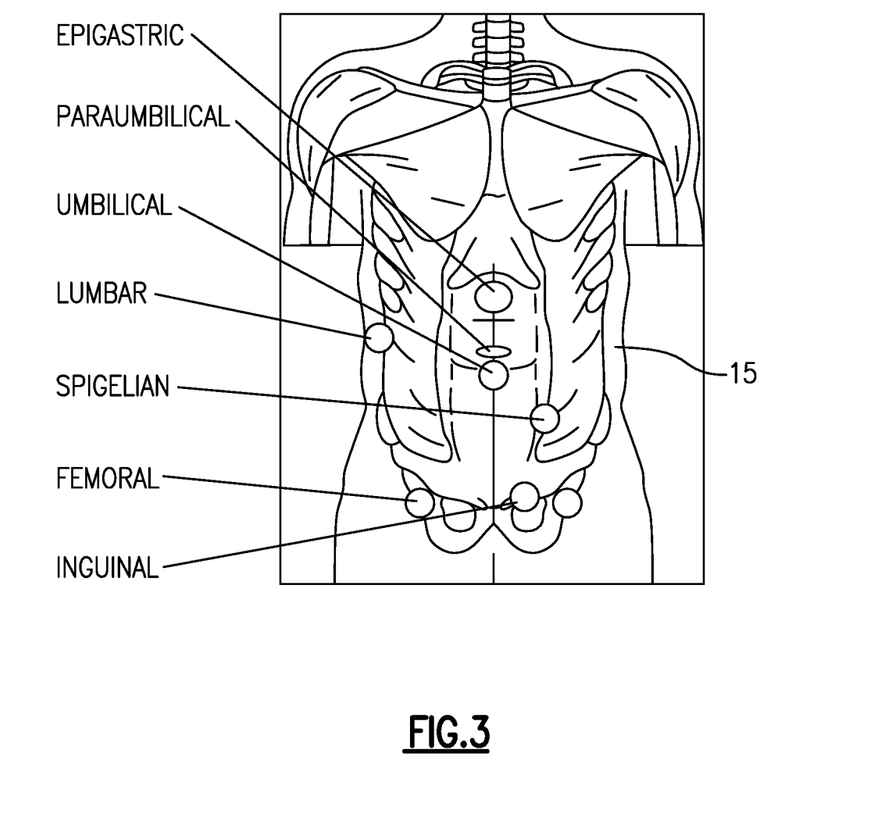
FIG. 3 is a schematic view showing typical hernia locations.

See FIG. 3. which shows typical locations for hernias in the abdominal and mid-torso regions of a human body 15.

Hernias may be treated surgically, with the physician reducing the herniated tissue and then bolstering the containing tissue. This may be accomplished using a suturing technique. However, in many cases suturing is not adequate, and it is necessary to use a mesh in order to bridge the closure and reduce the tension applied to the containing tissue. The mesh may be placed outboard of the defect, inboard of the defect, or both. The mesh is typically secured in place using sutures and/or surgical staples.

Ligament, Tendon and/or Muscle Repair

Figure 4:
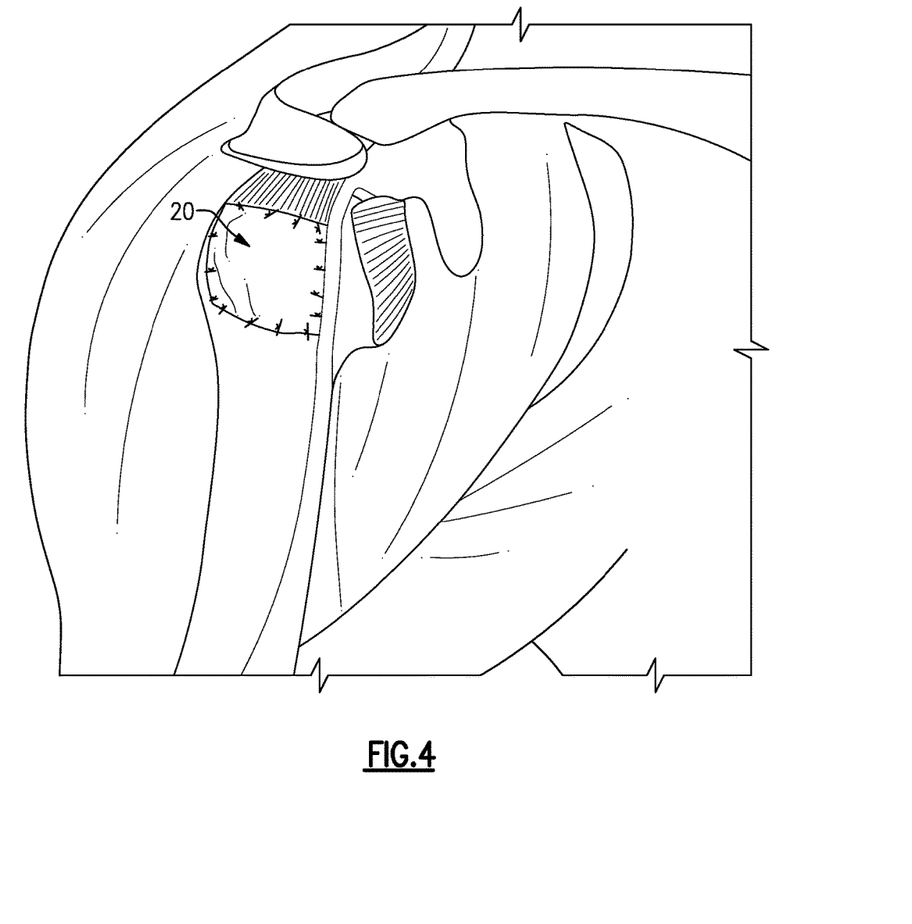
FIG. 4 is a schematic view showing the repair of a rotator cuff with reinforcing matrix.

Meshes are also used to surgically repair and/or reinforce ligaments, tendons and/or muscles. By way of example but not limitation, meshes are commonly used to repair and/or reinforce the rotator cuff of the shoulder, the Achilles tendon in the heel, and other ligaments, tendons and/or muscles throughout the body (e.g., the joint capsule of the hip, the joint capsule of the knee, etc.). These tissues may be injured or weakened due to trauma and/or degradation. Primary repair of the tissue may be effected with sutures to re-approximate the anatomy; however, these re-approximated tissues often fail to heal biologically, and the sutures may pull through the re-approximated tissue. In these situations, a mesh may be used to reinforce the repair. The mesh may be laid over the tissue, or wrapped around the tissue, and then sutured into place. The mesh then takes up some of the load, thereby limiting stress on the damaged tissue during healing. See FIG. 4, which shows a mesh 20 being used in the repair of a torn rotator cuff in the shoulder.

Chronic Ulcerations

Chronic ulcerations are typically wounds that do not heal. Chronic ulcerations are often caused by poor circulation, cardiovascular disorders, diabetes and/or external pressure (e.g., due to chronic confinement in a wheelchair, bed, etc.). By way of example but not limitation, chronic diabetic foot ulcers occur in up to 15% of the diabetic population.

There are many treatment options for chronic ulcerations. By way of example but not limitation, chronic ulcerations may be treated with a negative pressure treatment. With this approach, excess fluid and cellular waste (which usually prolongs the inflammatory phase of wound healing) is removed with negative pressure. Chronic ulcerations may also be treated with hyperbaric oxygen. Chronic ulcerations are also frequently treated using a mesh—with this approach, the mesh is applied to the wound and provides a scaffold for cells to re-populate the injured tissue, lay down new extracellular matrix and eventually heal the ulcer.

Mesh Properties

A wide variety of meshes are currently available. The properties of a particular mesh may vary according to its specific application; however, the important properties of the mesh generally include:

Tensile Strength

The mesh must be able to withstand the physiological tension that the underlying tissue will experience during anticipated activity. By way of example but not limitation, with abdominal hernia repairs, the mesh must be able to withstand the intra-abdominal pressures associated with coughing and jumping. These are estimated to be approximately 180 mm Hg for the typical patient. By way of further example but not limitation, with torn rotator cuff repairs, the mesh must be able to withstand the contractile forces of the muscle/tendon during a normal range of motion.

Pore Size

Pore size is an extremely important characteristic of the mesh, since it affects how the mesh will interact with the underlying tissue. Pore size should generally not be smaller than about 75 µm, since any pore smaller than that generally does not allow macrophages, fibroblasts, blood vessels, collagen, etc. to infiltrate the mesh. Larger pores allow for more soft tissue to grow within the mesh, and also increase the flexibility of the mesh as a whole.

Weight

The weight of the mesh is generally defined by the properties of the base material, the pore size, and the thickness of the members making up the mesh. Weights are generally broken down into two categories:

Heavy-Weight: >100 g/m$^2$, and generally characterized by small pores and high tensile strength, eliciting a strong tissue reaction and typically resulting in dense tissue scarring.

Light-Weight: ~33 g/m$^2$, and generally characterized by larger pores and a more elastic nature, capable of withstanding significant abdominal pressures.

Biocompatibility

The mesh must be made of a biocompatible material.

Elasticity

The mesh must be able to conform to the motion of the underlying tissue and physiology. For the abdominal wall, the elasticity of the mesh should generally be about 35%.

Adhesions

Adhesions are fibrous bands that connect the mesh to the underlying tissue. Heavy-weight meshes are generally associated with more robust adhesions than light-weight meshes.

SUMMARY OF THE INVENTION

The present invention comprises a novel spacer fabric mesh for use in tissue engineering applications. Spacer fabrics are porous three-dimensional, woven or knit structures which comprise a discrete bottom fabric layer, a discrete top fabric layer, and a discrete intermediate layer comprising a plurality of interconnecting fibers which extend between, and connect, the bottom layer and the top layer. By forming the novel spacer fabric mesh out of a porous three-dimensional spacer fabric, tissue can grow not only into the bottom layer and top layer of the spacer fabric, but also deep within the voluminous interior of the spacer fabric (i.e., the intermediate layer where the interconnecting fibers extend between the bottom layer and the top layer), whereby to provide enhanced tissue in-growth. Furthermore, by varying the composition and geometry of the fibers, the mesh pattern and pore size of the bottom layer and the top layer, the orientation and spacing of the interconnecting fibers of the intermediate layer, and the thicknesses of the bottom layer, top layer and intermediate layer, the spacer fabric mesh can be tuned by layer so as to provide a superior construction not achievable with a conventional two-dimensional mesh.

If desired, the spacer fabric mesh may include cells, biologically-active agents and/or pharmaceuticals so as to facilitate tissue engineering. If desired, such cells, biologically-active agents and/or pharmaceuticals may be disposed within the voluminous interior of the spacer fabric (i.e., the intermediate layer where the interconnecting fibers extend between the bottom layer and the top layer) so as to shield them from detrimental processes commonly encountered during the preparation and insertion of meshes.

In one preferred form of the invention, there is provided a spacer fabric mesh comprising:
a spacer fabric comprising:
a bottom fabric layer;
a top fabric layer; and
an intermediate layer comprising a plurality of interconnecting fibers which extend between, and connect, said bottom layer and said top layer, wherein said interconnecting fibers have sufficient resilience and stiffness to keep said bottom layer and said top layer separated when pressure is applied to at least one of said bottom layer and said top layer.

In another preferred form of the invention, there is provided a method for treating a patient, the method comprising:
providing a spacer fabric mesh comprising:
a spacer fabric comprising:
a bottom fabric layer;
a top fabric layer; and
an intermediate layer comprising a plurality of interconnecting fibers which extend between, and connect, said bottom layer and said top layer, wherein said interconnecting fibers have sufficient resilience and stiffness to keep said bottom layer and said top layer separated when pressure is applied to at least one of said bottom layer and said top layer; and
positioning said spacer fabric mesh in the patient.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Spacer Fabrics in General

Spacer fabrics are porous three-dimensional, woven or knit structures which were developed to address the inadequacies of foams. Spacer fabrics generally comprise three distinct layers (i.e., a bottom fabric layer, a top fabric layer, and an intermediate layer which comprises a plurality of interconnecting fibers which extend between, and connect, the top layer with the bottom layer) and are characterized by a three-dimensional porous structure having good breathability, wettability, and resilient crush resistance. Spacer fabrics are manufactured using knitting or weaving techniques, are elastic in nature, and have been employed in many applications where resilient support is required, e.g., clothing, mattresses, seats, supports, etc.

Figure 5:
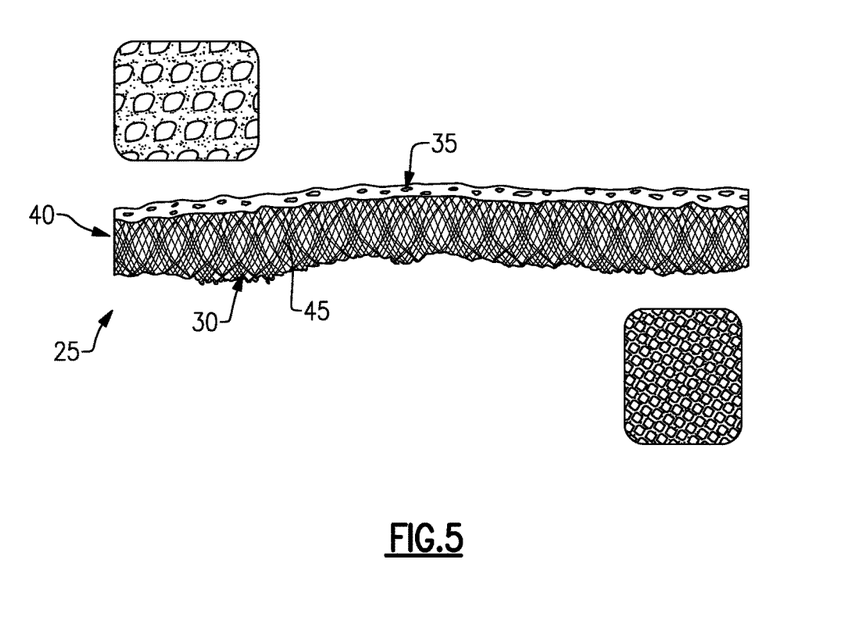
FIGS. 5 and 6 are schematic views a spacer fabric construct.
Figure 6:
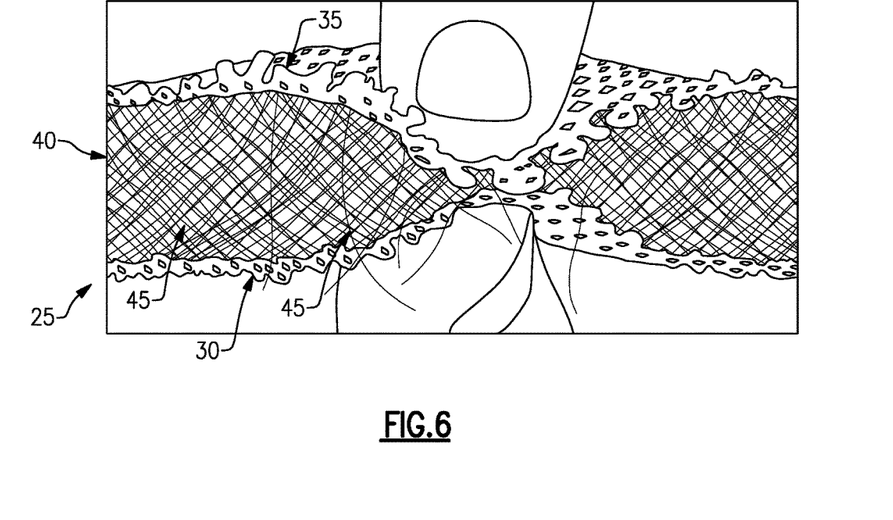

Looking now at FIGS. 5 and 6, there is shown a three-dimensional knit spacer fabric 25. Spacer fabric 25 comprises a discrete bottom fabric layer 30, a discrete top fabric layer 35, and a discrete intermediate layer 40 comprising a plurality of interconnecting fibers 45 which extend between, and connect, bottom layer 30 and top layer 35. A portion of the interconnecting fibers 45 are substantially perpendicular with respect to each of the bottom layer 30 and top layer 35, while the remaining interconnecting fibers 45 are disposed at an acute angle between bottom layer 30 and top layer 35. The interconnecting fibers 45 extending between bottom layer 30 and top layer 35 have sufficient resilience and stiffness to keep bottom layer 30 and top layer 35 separated when pressure is applied to either bottom layer 30, top layer 35 or both bottom layer 30 and top layer 35.

Knit manufacturing is the most common method for producing spacer fabrics. The double-faced spacer fabric 25 is prepared by knitting a three-dimensional knit fabric structure on a double-needle bar warp knitting machine commonly used in the manufacture of velvet. The fibers which are used to knit the spacer fabric are typically a synthetic material such as polyester, acrylic or nylon. The fibers may be a filament or spun, textured or fully-oriented. As noted above, the interconnecting fibers 45 extending between bottom fabric layer 30 and top layer 35 have sufficient resilience and stiffness to keep bottom layer 30 and top layer 35 separated when pressure is applied to either bottom layer 30, top layer 35 or to both bottom layer 30 and top layer 35.

Bottom layer 30 and top layer 35 may be formed out of the same or different base materials, may have the same or different fiber diameters, may have the same or different mesh pattern, and may have the same or different pore sizes.

The interconnecting fibers 45 of intermediate layer 40 can be made of the same or different base material as those used in bottom layer 30 and/or top layer 35. Among other things, in order to render the interconnecting fibers 45 resilient, the fibers may be made of a resilient material such as a monofilament or multifilament polyester or nylon. If desired, the interconnecting fibers 45 can be made of a superelastic material, e.g., shape memory polymers or nickel-titanium (Nitinol) wire.

Figure 7:
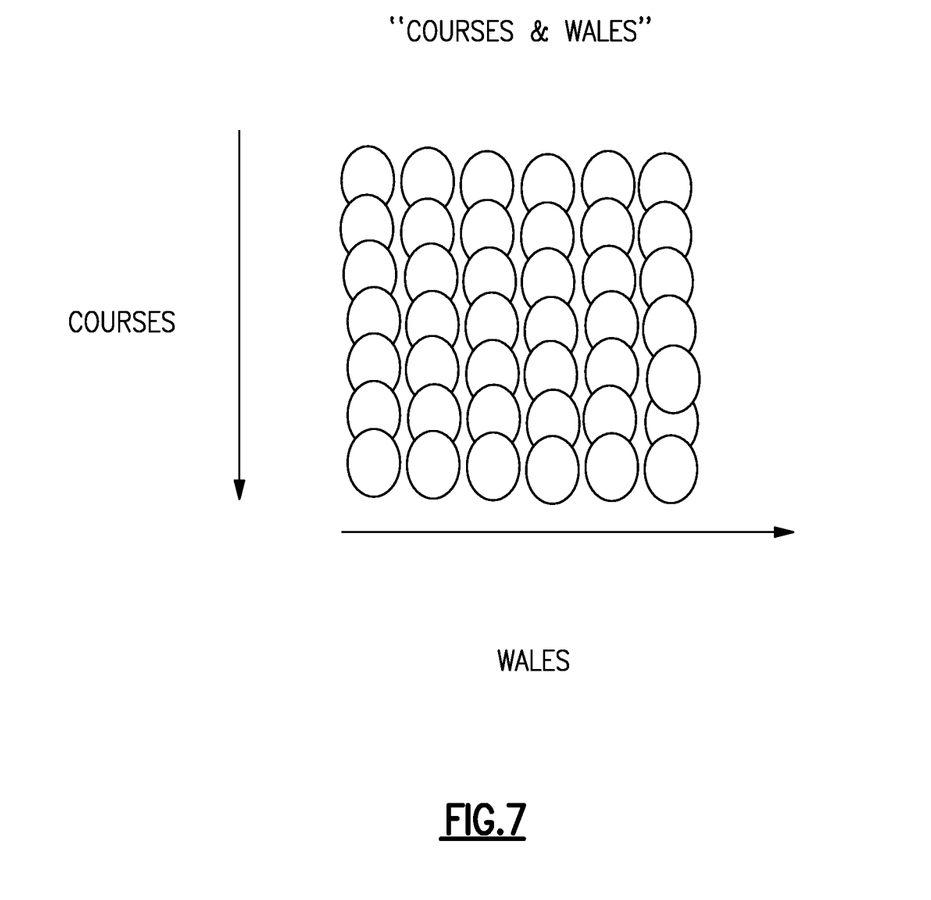
FIG. 7 is a schematic view showing the knit pattern of a spacer fabric.

By appropriately selecting (i) the composition and geometry of the fibers, (ii) the mesh pattern and pore size of bottom layer 30 and top layer 35, (iii) the orientation and spacing of the interconnecting fibers 45 of intermediate layer 40, and (iv) the thickness of bottom layer 30, top layer 35 and intermediate layer 40, the material properties of spacer fabric 25 can be controlled. By way of example but not limitation, a thicker overall spacer fabric manufactured using thinner filaments is generally more compliant than a thinner overall spacer fabric manufactured from thicker filaments. By way of further example but not limitation, the pore sizes of bottom layer 30 and top layer 35 can be adjusted by changing the needle spacing and the thickness of the fiber used. By way of further example but not limitation, it is possible to adjust the size of the knit pattern (sometimes referred to as "Courses & Wales") on one or both of bottom layer 30 and top layer 35. See FIG. 7.

Thus, spacer fabrics address many of the inadequacies of traditional foams. The highly porous nature of spacer fabrics allows them to have excellent fluid flow and thermal properties. Spacer fabrics are highly tailorable to specific applications, and are cost efficient since they are made from a low cost starting material.

Spacer Fabric Mesh for Use in Tissue Engineering Applications

The present invention comprises the provision and use of a novel spacer fabric mesh for use in tissue engineering applications. As noted above, and as will be discussed in further detail below, spacer fabrics generally comprise three distinct layers (i.e., a bottom layer, a top layer, and an intermediate layer which connects the top layer with the bottom layer) and are characterized by a three-dimensional porous structure having good breathability, wettability, and resilient crush resistance. The present invention provides a mesh comprising a spacer fabric, whereby to provide a superior mesh having a three-dimensional porous structure characterized by superior breathability, wettability, and resilient crush resistance.

Figure 8:
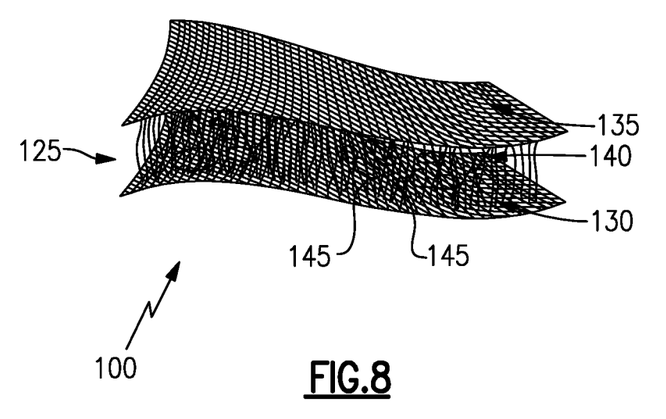
FIG. 8 is a schematic view showing a spacer fabric mesh formed in accordance with the present invention.

More particularly, and looking now at FIG. 8, there is shown a mesh 100 formed in accordance with the present invention. Mesh 100 comprises a three-dimensional woven or knit spacer fabric 125. Spacer fabric 125 comprises a discrete bottom fabric layer 130, a discrete top fabric layer 135, and a discrete intermediate layer 140 comprising a plurality of interconnecting fibers 145 which extend between, and connect, bottom layer 130 and top layer 135. A portion of interconnecting fibers 145 are substantially perpendicular with respect to each of the bottom layer 130 and top layer 135, while the remaining interconnecting fibers 145 are disposed at an acute angle between bottom layer 130 and top layer 135. The interconnecting fibers 145 extending between bottom layer 130 and top layer 135 have sufficient resilience and stiffness to keep bottom layer 130 and top layer 135 separated when pressure is applied to either bottom layer 130, top layer 135 or to both bottom layer 130 and top layer 135.

By appropriately selecting (i) the composition and geometry of the fibers, (ii) the mesh pattern and pore size of bottom layer 130 and top layer 135, (iii) the orientation and spacing of the interconnecting fibers 145 of intermediate layer 140, and (iv) the thickness of bottom layer 130, top layer 135 and intermediate layer 140, the material properties of spacer fabric 125 (and hence mesh 100) can be controlled. By way of example but not limitation, a thicker overall spacer fabric 125 manufactured using thinner filaments is generally more compliant than a thinner overall spacer fabric manufactured from thicker filaments. By way of further example but not limitation, the pore sizes of bottom layer 130 and top layer 135 can be adjusted by changing the needle spacing and the thickness of the fiber used. By way of further example but not limitation, it is possible to adjust the size of the knit pattern (sometimes referred to as "Courses & Wales") on one or both of bottom layer 130 and top layer 135.

Spacer fabric 125 of mesh 100 may be made from any fiber or fibers appropriate for tissue engineering applications. By way of example but not limitation, the following absorbable and non-absorbable polymers may be used:

Polyglactin (for an absorbable mesh)
Polyglycolic acid (for an absorbable mesh)
Polypropylene (for a non-absorbable mesh)
Polyester (for a non-absorbable mesh)
ePTFE (for a non-absorbable mesh)

Spacer fabric 125 of mesh 100 can also be made from a combination of polymeric and non-polymeric materials. By way of example but not limitation, Shape Memory Alloy (SMA) fibers can be knit, woven, or sewn into the three-dimensional spacer fabric structure. The SMA fibers can help with the deployment and positioning of the mesh during the surgical procedure, specifically during a minimally invasive surgical procedure, due to their enhanced elasticity. The metallic SMA fibers (e.g., Nitinol) can also help to increase the strength and stiffness of the spacer fabric construct when compared to a polymer spacer fabric. The spacer fabric can be constructed out of a combination of SMA and polymeric fibers. Biologic fibers may also be used to produce the spacer fabric. These biologic fibers may be silk fibers, collagen fibers, elastin fibers, etc. These biologic fibers may be used alone, or in combination with, polymeric and non-polymeric fibers, so as to enhance tissue integration.

Bottom layer 130 and top layer 135 may be formed out of the same or different base materials, may have the same or different fiber diameters, may have the same or different mesh pattern, and may have the same or different pore sizes.

Thus, if desired, the two faces of spacer fabric 125 may be made of different materials, e.g., one face may be made of an absorbable material and the other face may be made of a permanent material, and/or one face may be made of stronger material and the other face made of a more adhesion-resistant material.

The interconnecting fibers 145 of intermediate layer 140 can be made of the same or different base material as that used in bottom layer 130 and/or top layer 135. Among other things, in order to render the interconnecting fibers 140 resilient, the fibers may be made of resilient material such as a monofilament or multifilament polyester or nylon. If desired, the interconnecting fibers 140 can be made of a superelastic material, e.g., shape memory polymers or nickel-titanium (Nitinol) wire.

Porosity of the mesh is the main determinant of tissue reaction to the mesh. Pores must generally be more than 75 µm in diameter in order to allow infiltration by macrophages, fibroblasts, blood vessels, collagen, etc. Meshes with larger pore sizes allow increased soft tissue in-growth, and provide a more flexible repair due to the avoidance of granuloma bridging. Granulomas normally form around individual mesh fibers as part of the foreign body reaction. Individual granulomas become confluent with each other and encapsulate the entire mesh. This leads to a stiff scar plate and reduced flexibility. A stiff scar plate and reduced flexibility tends to occur in meshes having small pore sizes of less than 800 µm.

Figure 9:
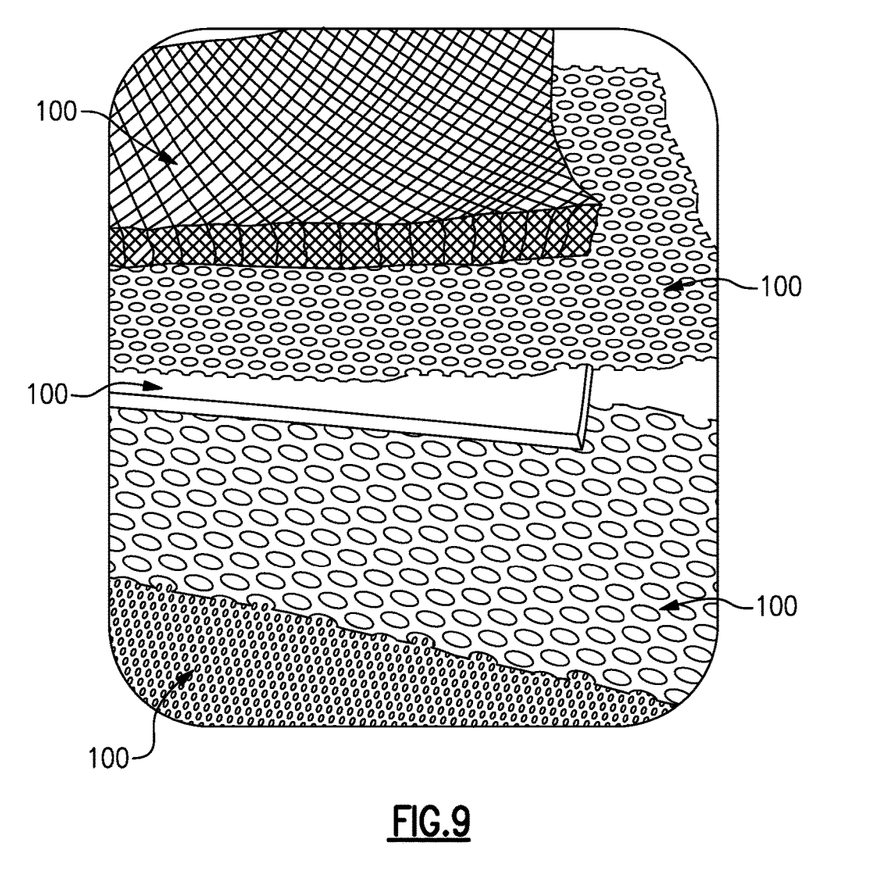
FIG. 9 is a schematic view showing a plurality of spacer fabric meshes formed in accordance with the present invention.

In one preferred form of the invention, mesh 100 comprises a spacer fabric 125 having an overall porosity ranging from about 10% to about 98%, with pore sizes ranging from about 100 to about 5000 microns, depending on the application. The pore sizes of the top and bottom layers can be altered by changing the needle spacing and the thickness of the fiber. See, for example, FIG. 9, which shows a variety of different meshes 100.

The diameter of the starting fiber(s) greatly determines the mechanical properties of the final mesh structure. Thicker fibers result in a stiffer final construct. The upper limit for the fiber diameter is determined by the knitting machine being used. Preferably, the diameter of the fiber is between about 0.05 inch and about 0.0002 inch. Most preferably, the diameter of the fiber is between about 0.01 inch and about 0.003 inch.

Figure 10:
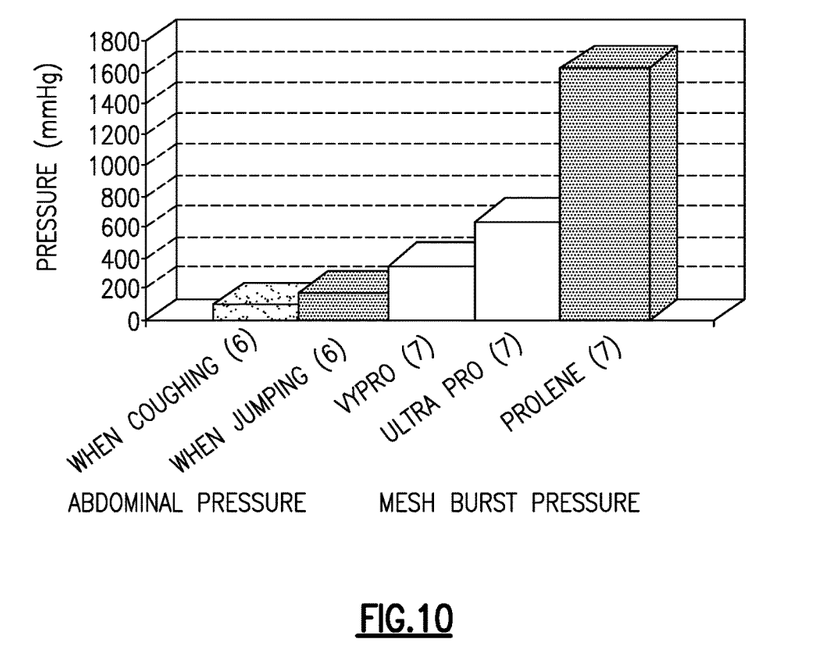
FIG. 10 is a schematic view showing abdominal pressure under normal physiologic functions and mesh burst pressure for various types of hernia meshes.

The maximum intra-abdominal pressures generated in healthy adults occur during coughing and jumping. These are estimated to be about 170 mm Hg. Three-dimensional meshes which are used to repair large hernias therefore need to withstand at least 180 mm Hg before bursting (tensile strength up to 32 N/cm$^2$). See FIG. 10.

The weight of the mesh depends on both the weight of the material used to construct the mesh and the amount of material used (which is influenced by pore size). Heavy-weight meshes generally utilize thick polymers, have small pore sizes and high tensile strength. These heavy-weight meshes typically weigh 100 g/m$^2$ (1.5 g for 10×15 cm mesh). The strength of a heavy-weight mesh is derived from a large mass of material, which in turn causes a profound tissue reaction and dense scarring.

Light-weight meshes utilize thinner filaments and have larger pores (>1 mm). Their weight is typically 33 g/m$^2$ (0.5 g for 10×15 cm mesh). Light-weight meshes initiate a less pronounced foreign body reaction than heavy-weight meshes and are more elastic. Despite a reduced tensile strength, light-weight meshes can still withstand pressures above the maximum abdominal pressure of 170 mm Hg (minimum tensile strength 16 N/cm$^2$).

A new generation of even lighter meshes include titanium/propylene composite meshes. Titanium/propylene composite meshes have been shown to be associated with a more rapid recovery from surgery. The lightest of these (i.e., Extralight TiMesh) may have insufficient tensile strength in some situations (maximum tensile strength 12 N/cm$^2$). Three-dimensional spacer fabrics can be made with optimal ultra-light meshes and utilize the vertical spacer fibers to increase the columnar strength of the construct (increased compression, buckling and torsional strength levels).

The highly porous nature of the spacer fabric mesh can also be utilized as a drug delivery device. Prior to implantation, the pores of the mesh can be impregnated with cells, biologically-active agents and/or pharmaceuticals. For example, the mesh can be impregnated with a bone morphogenetic protein, BMP-2, and used as an adjunct to rotator cuff repair. The BMP-2 is localized at the site in need of repair.

Figure 11:
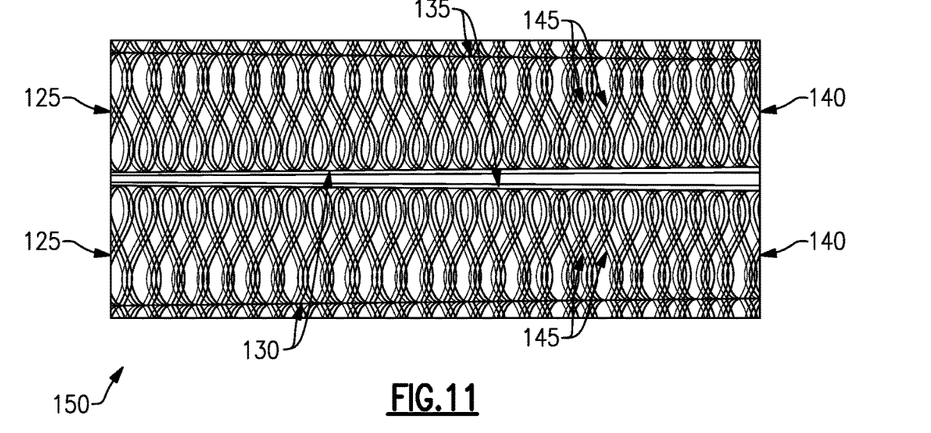
FIG. 11 is a schematic view showing a multi-layer spacer fabric mesh comprising a plurality of spacer fabric constructs.

It should also be appreciated that, if desired, a mesh 150 may be formed by stacking two or more pre-formed spacer fabric constructs, one on top of another, so as to form a multi-level spacer fabric construct. See FIG. 11, which shows a mesh 150 formed by stacking two spacer fabric constructs 125 one on top of another, where each spacer fabric construct 125 comprises a bottom layer 130, a top layer 135 and an intermediate layer 140, wherein intermediate layer 140 comprises a plurality of fibers 145 which extend between, and connect, bottom layer 130 and top layer 135. Alternatively, a multi-level spacer fabric construct 150 may be knit using specialized equipment.

Forming mesh 100 out of a spacer fabric 125 provides numerous advantages over conventional meshes.

As noted above, spacer fabrics generally comprise three distinct layers (i.e., a bottom layer, a top layer, and an intermediate layer which connects the top layer with the bottom layer) and are characterized by a three-dimensional porous structure having good breathability, wettability, and resilient crush resistance. The present invention provides a mesh formed out of spacer fabric, whereby to provide a superior synthetic mesh having a three-dimensional porous structure characterized by good breathability, wettability, and resilient crush resistance.

Furthermore, by appropriately selecting (i) the composition and geometry of the fibers, (ii) the mesh pattern and pore size of bottom layer 130 and top layer 135, (iii) the orientation and spacing of the interconnecting fibers 145 of intermediate layer 145, and (iv) the thickness of bottom layer 130, top layer 135 and intermediate layer 140, the material properties of spacer fabric 125 (and hence mesh 100) can be controlled. By way of example but not limitation, a thicker overall spacer fabric manufactured using thinner filaments is generally more compliant than a thinner overall spacer fabric manufactured from thicker filaments. By way of further example but not limitation, the pore sizes of the bottom layer 130 and top layer 135 can be adjusted by changing the needle spacing and the thickness of the fiber used. By way of further example but not limitation, it is possible to adjust the size of the knit pattern (sometimes referred to as "Courses & Wales") on one or both of bottom layer 130 and top layer 135.

A mesh formed out of spacer fabric also provides additional advantages over conventional two-dimensional meshes.

Three-Dimensional Tissue Ingrowth.

A mesh formed out of a three-dimensional spacer fabric is advantageous over a traditional two-dimensional mesh because spacer fabrics comprise true three-dimensional pores for cells to infiltrate, populate, lay down new extracellular matrix, and eventually develop into healed tissue. More particularly, traditional meshes are effectively two-dimensional structures, meaning that tissue can grow onto the surface of the mesh but cannot infiltrate significantly into the mesh, thus limiting true bio-integration of the mesh with the native anatomy. With the present invention, true three-dimensional integration is achieved.

Additionally, and as noted above, the two faces of the three-dimensional mesh can be made of different materials, and knit with different pore sizes, so as to better accommodate the tissue which each face comes into contact with. By way of example but not limitation, one face can be made of a non-resorbable polyester mesh so as to provide a face of enhanced strength, the second face can be made by a resorbable hydrophilic film which provides a temporary barrier, minimizing long-term tissue attachment, with the first face being attached to the second face by means of vertical or perpendicular interconnecting polyester fibers 145 which create the space/volume for deep and complete tissue in-growth.

Unlike traditional two-dimensional meshes, meshes formed out of three-dimensional spacer fabrics fill an appreciable volume. Thus they also find significant utility in situations where bulk tissue needs to be created. In other words, instead of simply using a flat, two-dimensional mesh within a large void or volume, a mesh formed out of a relatively thick, three-dimensional spacer fabric can be employed so as to fill three-dimensional space. By way of example but not limitation, in the case of diabetic foot ulcers, where wounds may extend deep into the foot, a three-dimensional spacer fabric can be used to fill the void remaining after necrotic tissue has been removed, and the spacer fabric can serve as a scaffold for cellular re-population and remodeling. Additionally, by filling these voids with the three-dimensional synthetic mesh, a more even pressure distribution is established at the wound surface, thereby eliminating high pressure regions and minimizing the risk of repeat ulceration.

Improved Mechanical Strength.

Synthetic meshes are generally physically and chemically inert, i.e., they are stable, non-immunogenic and non-toxic. However, synthetic meshes are generally not biologically inert, i.e., a foreign body reaction is typically triggered by their presence within the body. This involves inflammation, fibrosis, calcification, thrombosis and formation of granulomas.

The foreign body reaction is generally similar regardless of the type of material introduced into the body, but the extent of the foreign body reaction may vary according to the type of material introduced into the body, the amount of material introduced into the body, and the configuration of the material introduced into the body. By way of example but not limitation, for synthetic meshes, pore size can affect the foreign body reaction, i.e., meshes with small pores tend to develop stiff scar plates whereas meshes with larger pores tend to have a gap between the scar tissue.

Synthetic meshes also appear to alter collagen composition at the repair site. More particularly, during normal healing, the initial, immature Type III collagen is rapidly replaced by stronger Type I collagen. This process is typically delayed in the presence of a foreign body such as a synthetic mesh. As a result, the collagen composition at the repair site is altered, with the new collagen having a much lower ratio of Type I collagen to Type III collagen. This can reduce mechanical stability at the repair site.

By providing a synthetic mesh formed out of a three-dimensional spacer fabric, extra columnar volume is provided for the tissue to grow into. As a result, if the foreign body reaction should cause altered collagen composition at the repair site (e.g., a lower ratio of Type I collagen to Type III collagen, leading to reduced mechanical stability), the vertical, interconnecting spacer fabric fibers 145 can provide the necessary mechanical stability while acting as a three-dimensional scaffold for tissue infiltration, whereby to improve composite strength levels.

Applications for Spacer Fabric Meshes for Tissue Engineering

Oral and maxillofacial surgery
Craniofacial surgery

Tooth Anchor
Dental void fillers
Breast reconstruction
Abdominal wall repair
Repair of chest wall defect
Pelvic reconstructive surgery
Puncture, burn and other wound treatment
Reconstructive surgery not otherwise identified above
Cosmetic surgery not otherwise identified above
Rotator Cuff repair
Anterior Shoulder Capsule
Flex/Extensor Tendon
Ulnar Collateral Ligament repair
Achilles Tendon Repair
Lateral Ankle Complex
Chronic Diabetic Foot Ulcers Modifications of the Preferred Embodiments It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A spacer fabric mesh comprising:
 a spacer fabric comprising:
  a bottom fabric layer;
  a top fabric layer; and
  an intermediate layer comprising a plurality of interconnecting fibers which extend between, and connect, said bottom fabric layer and said top fabric layer, wherein said interconnecting fibers are made of a shape memory alloy, and said bottom fabric layer, said top fabric layer, and said intermediate layer are each discrete layers that are separate from one another, wherein a first portion of said interconnecting fibers extend substantially perpendicular to said bottom fabric layer and said top fabric layer, while a second portion of said interconnecting fibers are disposed at an acute angle relative to said bottom fabric layer and said top fabric layer.

2. The spacer fabric mesh according to claim 1 wherein said spacer fabric comprises a material selected from the group consisting of Polyglactin, Polyglycolic Acid, Polypropylene, Polyester, ePTFE, Collagen, Elastin, and Silk.

3. The spacer fabric mesh according to claim 1 wherein said interconnecting fibers are monofilament.

4. The spacer fabric mesh according to claim 1 wherein said interconnecting fibers are multifilament.

5. The spacer fabric mesh according to claim 1 wherein said spacer fabric mesh comprises at least two spacer fabric structures stacked one on top of another to form a multi-level spacer fabric mesh.

6. The spacer fabric mesh according to claim 1 wherein said bottom fabric layer and said top fabric layer comprise the same material.

7. The spacer fabric mesh according to claim 1 wherein said bottom fabric layer and said top fabric layer comprise different materials.

8. The spacer fabric mesh according to claim 1 wherein said shape memory alloy is characterized by superelasticity.

9. The spacer fabric mesh according to claim 1 wherein said spacer fabric further comprises polymeric fibers in addition to said shape member alloy fibers.

10. The spacer fabric mesh according to claim 1 wherein the spacer fabric mesh has a pore size of between 0.3 mm and 5.0 mm.

11. The spacer fabric mesh according to claim 1 wherein said interconnecting fibers have a diameter of between 0.02 mm and 0.5 mm.

12. The spacer fabric mesh according to claim 1 wherein said spacer fabric mesh has a maximum tensile strength of 12 N/cm$^2$ and said interconnecting fibers are employed to increase the columnar rigidity and strength of the spacer fabric mesh.

13. The spacer fabric mesh according to claim 1 wherein one of said bottom fabric layer and said top fabric layer comprises a non-resorbable polyester, and further wherein the other of said bottom fabric layer and said top fabric layer comprises a resorbable hydrophilic film which minimizes tissue attachment.

14. The spacer fabric mesh according to claim 1, wherein said bottom fabric layer and said top fabric layer include different mesh patterns.

15. The spacer fabric mesh according to claim 1, wherein said bottom fabric layer and said top fabric layer include different pore sizes.

16. The spacer fabric mesh according to claim 1, wherein one of said bottom fabric layer and said top fabric layer is made of an absorbable material and the other of said bottom fabric layer and said top fabric layer is made of a permanent material.

17. The spacer fabric mesh according to claim 1, wherein said interconnecting fibers have a diameter of between 0.01 inches and 0.003 inches.

18. The spacer fabric mesh according to claim 1, wherein said spacer fabric includes a porosity ranging from about 10% to about 98%, and includes pore sizes from about 100 microns to about 5000 microns.

19. The spacer fabric mesh according to claim 1, wherein said bottom fabric layer and said top fabric layer are outermost layers.

20. The spacer fabric mesh according to claim 1, wherein said spacer fabric includes only three layers.

21. The spacer fabric mesh according to claim 1, wherein said bottom fabric layer and said top fabric layer are both a knit fabric.

22. The spacer fabric mesh according to claim 1, wherein the intermediate layer prevents the bottom fabric layer and the top fabric layer from contacting.

23. The spacer fabric mesh according to claim 1, wherein said bottom fabric layer, said top fabric layer, and said intermediate layer are all a knit fabric.

24. A spacer fabric mesh comprising:
 a spacer fabric comprising:
  a bottom fabric layer;
  a top fabric layer wherein said bottom fabric layer and said top fabric layer are outermost layers; and
  an intermediate layer comprising a plurality of interconnecting fibers which extend between, and connect, said bottom fabric layer and said top fabric layer, wherein said interconnecting fibers are made of a shape memory alloy, said bottom fabric layer, said top fabric layer, and said intermediate layer are each discrete layers that are separate from one another, and said bottom fabric layer, said top fabric layer, and said intermediate layer are all a knit fabric, and said spacer fabric includes only three layers, wherein a first portion of said interconnecting fibers extend substantially perpendicular to said bottom fabric layer and said top fabric layer, while a second portion of said interconnecting fibers are disposed at an acute angle relative to said bottom fabric layer and said top fabric layer.

\* \* \* \* \*